United States Patent [19]

Török et al.

[11] Patent Number: 5,401,630
[45] Date of Patent: Mar. 28, 1995

[54] SPECIES-SPECIFIC DNA-DNA HYBRIDIZATION PROBE PREPARED USING CHROMOSOME SIZE DNA

[75] Inventors: Tamas Török, Albany; A. Douglas King, Jr., Martinez; David R. Rockhold, El Cerrito; Christina Royer, Oakland, all of Calif.

[73] Assignee: The United States of America as represented by the Secretary of Agriculture, Washington, D.C.

[21] Appl. No.: 695,167

[22] Filed: May 3, 1991

[51] Int. Cl.⁶ .......................... C12Q 1/68; C12Q 1/00; C07H 23/00; C12P 19/34
[52] U.S. Cl. ....................................... 435/6; 435/7.31; 435/81.1; 536/23.1; 536/24.3; 536/24.32; 536/24.33; 935/19; 935/77; 935/78
[58] Field of Search ..................... 435/6, 7, 7.31, 91.1, 435/91, 34; 536/23.1, 24.3, 24.32, 24.33; 935/19, 77, 78

[56] References Cited

U.S. PATENT DOCUMENTS

| | | | |
|---|---|---|---|
| 4,358,535 | 11/1982 | Falkow et al. | 435/5 |
| 4,683,195 | 7/1987 | Mullis et al. | 435/6 |
| 5,126,239 | 6/1992 | Livak et al. | 435/6 |

OTHER PUBLICATIONS

Carle et al. P.N.A.S. 82: 3756 (1985).
Chu et al. Science 234: 1582 (1986).
Vollarth et al. Nuclei. Acids. Res. 15 (19):7865 (1987).
Smith et al. Nucl. Acids Res. 15(11): 4 & 81 (1987).
C. L. Smith, T. Matsumoto, O. Niwa, S. Klco, J.-B. Fan, M. Yanagida and C. R. Cantor, "An Electrophoretic Karyotype for *Schizosaccharomyces pombe* by Pulsed Field Gel Electrophoresis," *Nucleic Acids Research* 15: 4481–4489 (1987).
J. R. Johnston, C. R. Contopouiou and R. K. Mortimer, "Karyotyping of Yeast Strains of Several Genera by Field Inversion Gel Electrophoresis," *Yeast* 4: 191–198 (1988).
M. J. Orbach, D. Vollrath, R. W. Davis and C. Yanofsky, "An Electrophoretic Karyotype of *Neurospora crassa*," *Molecular and Cellular Biology* 8: 1469–1473 (1988).
B. B. Magee, Y. Koltin, J. A. Gorman, and P. T. Magee, "Assignment of Cloned Genes to the Seven Electrophoretically Separated *Candida albicans* Chromosomes," *Molecular and Cellular Biology* 8: 4721–4726 (1988).
H. Brody and J. Carbon, "Electrophoretic Karyotype of *Aspergillus nidulans*," *Proceedings National Academy of Science USA* 86: 6260–6263 (1989).

*Primary Examiner*—Margaret Parr
*Assistant Examiner*—Miguel Escallon
*Attorney, Agent, or Firm*—M. Howard Silverstein; John D. Fado; Margaret A. Connor

[57] ABSTRACT

A species-specific DNA-DNA hybridization probe prepared using an isolated whole chromosome of a lower eukaryote as template. The probe is useful for the detection of conspecificity in lower eukaryotes selected from the group consisting of yeast and molds.

3 Claims, 5 Drawing Sheets

SPECIES-SPECIFIC DNA-DNA HYBRIDIZATION PROBE PREPARED USING CHROMOSOME SIZE DNA

BACKGROUND OF THE INVENTION

1. Field of the Invention

The invention relates to a species-specific DNA-DNA hybridization probe which is prepared using an isolated whole chromosome of a lower eukaryote as template. The probe is useful for the direction of conspecificity in lower eukaryotes.

2. Description of the Art

Identification of lower eukaryotic organisms is done by phenotypic characteristics. Using the genotype is a more stable identification method.

Yeast identification is a difficult yet needed scientific task. Accurate identification is required for epidemiology and identification of yeast-caused diseases and in the food industry where yeasts are a desired part of a given technology or cause spoilage.

Traditional technique for yeast identification is to perform morphological and physiological tests. These tests identify the cell shape and size as well as other characteristics. The physiological tests are based upon the ability of the organism to use certain chemicals and to grow in their presence or under anaerobic conditions to ferment them. In the two most universally used and thorough identification schemes, 50 to 100 tests are performed (J. A. Barnett et al., *Yeasts: Characteristics and Identification*, Cambridge University Press, 1983; N. J. W. Kreger van Rij (ed.), *Yeasts—A Taxonomic Study*, 3rd ed., Elsevier Science Publishers B.V., Amsterdam, in 1984). This testing can take up to six weeks. Computer programs have been developed to aid in the process of comparing test results with database entries for the almost 600 known species (J. A. Barnett et al., *Yeast Identification Program*, Cambridge University Press, Cambridge; American Society for Microbiology Computer User Group, 1989, Computer-Assisted Identification of Microorganisms, ASM, Washington, D.C.; T. Deak, 1990, *Yeast-ID*, University of Horticulture and Food Industry, Budapest). However, expertise on interpretation of the results is needed. Because of the amount of material required, the complexity of the tests and interpretation of the results, these tests are only done in specialized yeast laboratories or research laboratories.

Several commercial test kits for medically important yeasts have been developed and marketed. They are based upon the above mentioned reactions and are useful for disease identification. The number of medically important yeast species is limited; there are only about 50. Thus, it is relatively easy to create useful diagnostic kits for medical use. *Candida albicans*, the most important medical yeast is very often identified simply by germ tube formation. In the food industry almost 200 yeast species may occur, making identification more complex. No commercial test kits have been developed for this group of yeasts.

A newer development in the field of yeast identification was the reduction of the number of required tests (T. Deak, in A. D. King et al. (ed.), *Methods for the Mycological Examination of Food*, Plenum Publishing Co., New York, 1986; T. Deak et al., *Journal of Food Protection* 50: 243–264, 1987). The scheme was developed based upon a fairly even division of food-borne yeast species by the tests in question. In its final form, the simplified scheme uses about 25 tests to separate the 200 yeast species important in foods. A computer program has been developed to aid in the interpretation of the results.

In yeast taxonomy species differentiation is based upon interfertility. However, the establishment of conspecificity among homothallic and asporogenous yeasts and among industrially important, mostly aneuploids and/or polyploids, is rather hard on the basis of the phenotype. Comparisons between genotypic characteristics provide a more stabile classification. Thus, modern approaches analyze the G+C mol % (mol percent guanine and cytosine of DNA), the DNA homology by DNA-DNA re-association, and the DNA sequences coding for smaller rRNAs, etc.

DNA gel electrophoresis has been developed over the past several years. The development of pulsed field gel electrophoresis (PFGE) has permitted separation of relatively large pieces of DNA, even as large as chromosomes (Schwartz et al., *Cell* 37:67–75 (1984)). Contour clamped homogeneous electric field electrophoresis (CHEF) is one of the most recent developments of the basic PFGE (See Chu et al., *Science* 234: 1582–1585 (1986). CHEF allows for good resolution with preservation of sharp bands, straight lanes, and reproducible separation of DNA molecules up to 12–15 megabases. Some researchers have prepared probes using smaller than whole chromosome templates.

SUMMARY OF THE INVENTION

The invention comprises a species-specific DNA-DNA hybridization probe which is useful for assaying for conspecificity (belonging to the same species) in lower eukaryotes. The probe is prepared using isolated chromosome size DNA of a lower eukaryote as template. The templates are randomly primed with short chain primers in the presence of DNA polymerase and nucleotide mixture to produce the probe.

The assay comprises contacting the probe with a test sample comprising a denatured DNA chromosomal isolate under hybridization conditions such that DNA sequences in the test sample which are substantially homologous with the probe are hybridized to produce a hybridization product. The hybridization product is separated from unhybridized material by washing under conditions of low stringency, and the presence of DNA-DNA hybridization is detected as proof of conspecificity between the test strain and the strain from which the probe was prepared.

Probes prepared and used in accordance with the method of the invention provide taxonomically important information which can be used in areas such as medical diagnostics, food microbiology, and microbial systematics.

A probe kit which comprises the probe of the invention is useful for ready assay of test samples.

Other objects and advantages of this invention will become readily apparent from the ensuing description.

Figure 2A:
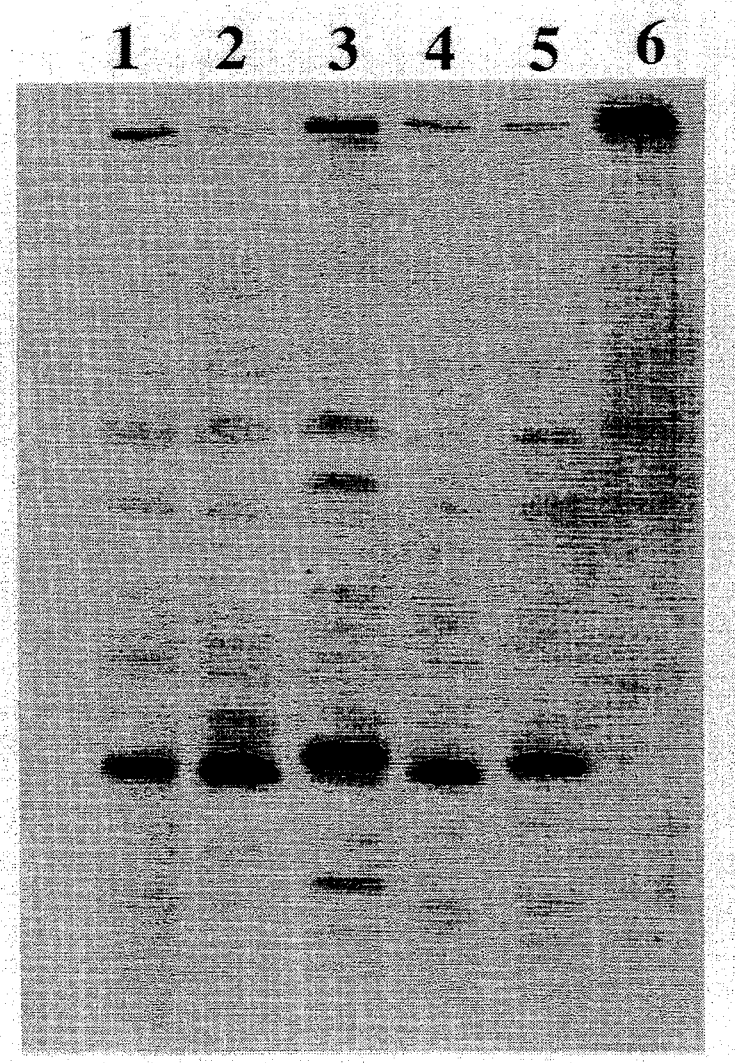
FIG. 2A is a Southern blot showing positive hybridization results in lanes 1–5, and no hybridization in lane 6. In the first 5 lanes chromosomes of different *S. cerevi-* siae strains were separated. In lane 6 there was a different species. The target and probe chromosome was chromosome V.
Figure 2B:
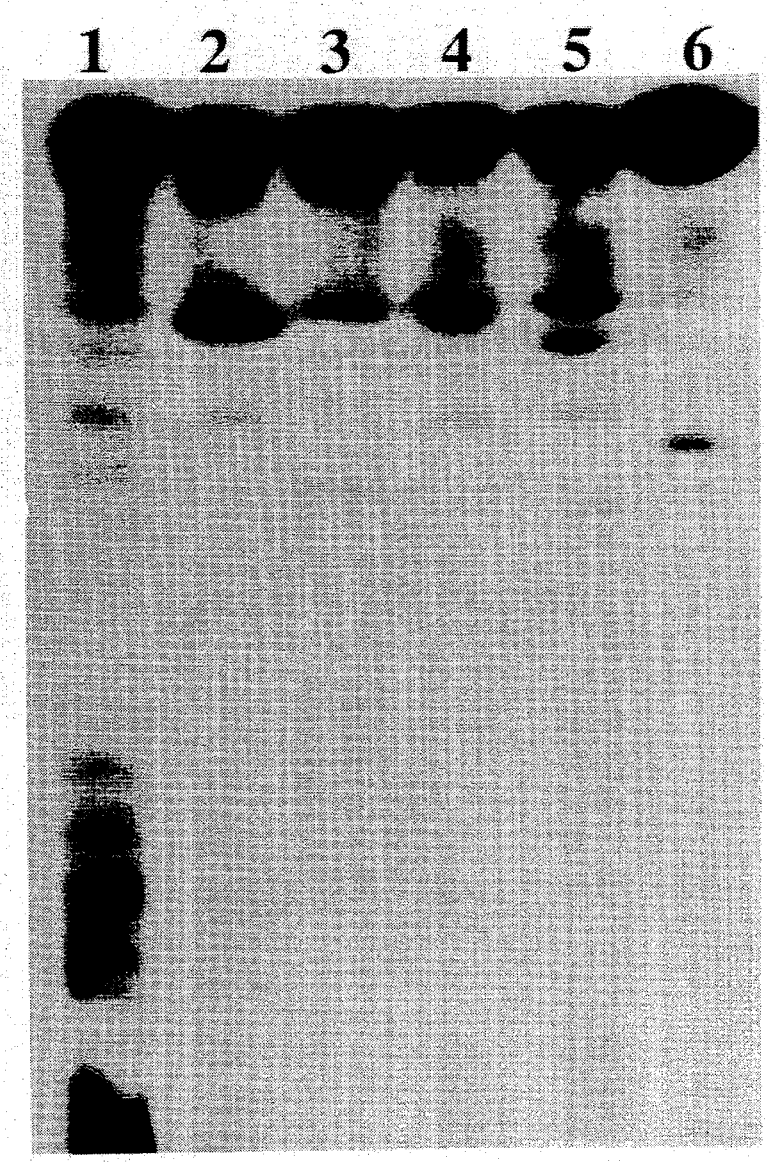

FIG. 2B is the same as FIG. 2A, except that the target and the probe chromosome was chromosome XII.

Figure 3A:
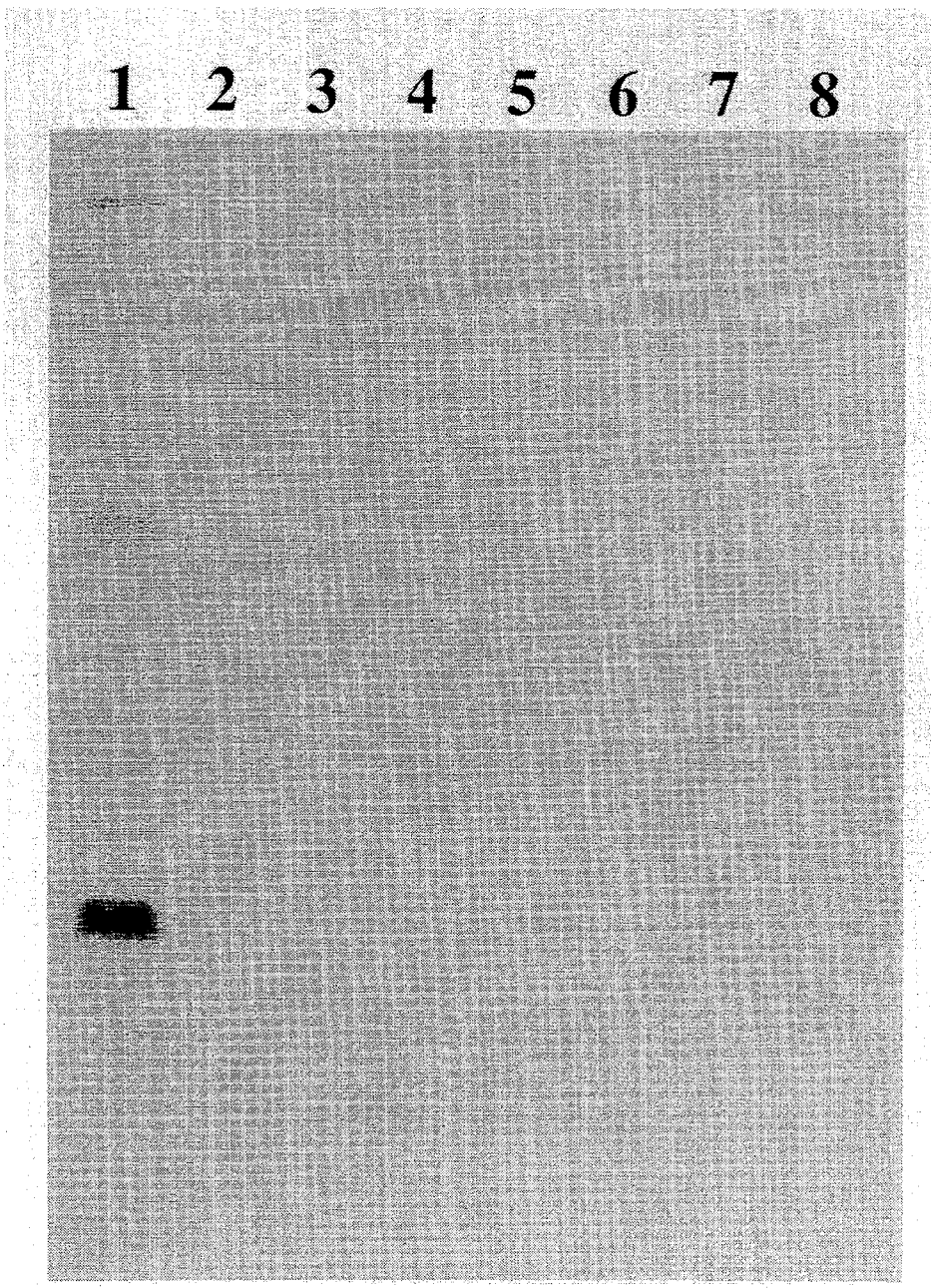

FIG. 3A is a Southern blot showing positive hybridization reaction in lane 1 for the control strain (*S. cerevisiae* YNN 295), and negative results for the lanes 2–6, where the chromosomes of different Zygosaccharomyces species were separated. The target and the probe chromosome was chromosome V.

Figure 3B:
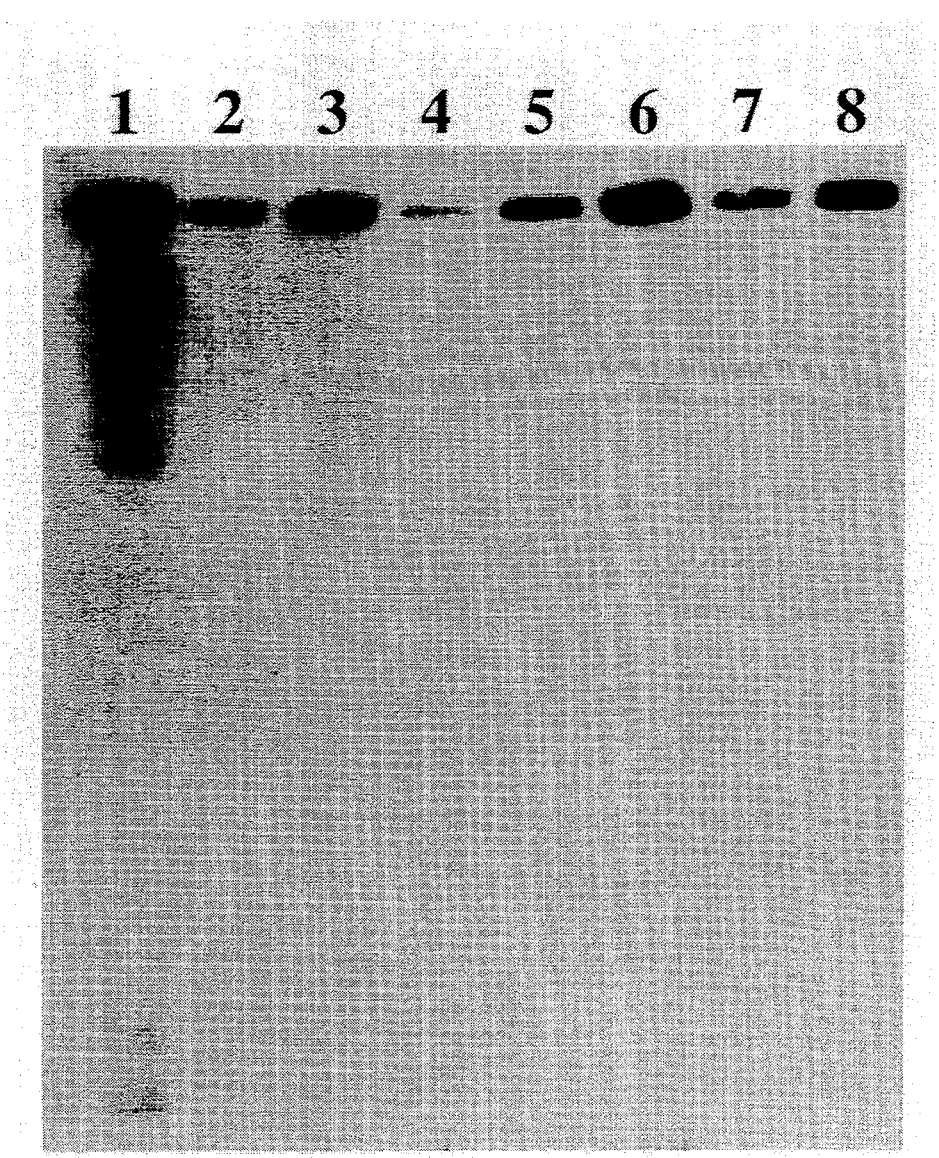

FIG. 3B is the same as FIG. 3A, except that the target and the probe chromosome was chromosome XII.

DETAILED DESCRIPTION OF THE INVENTION

The species-specific DNA-DNA hybridization probe of the invention is prepared using isolated chromosome size DNA of a lower eukaryote as template. The term "lower eukaryote" as used herein includes yeasts, molds, protozoa, and algae. The invention is further described with reference to yeast as the exemplary lower eukaryote.

Isolated chromosome size DNA of yeast is obtained as follows. First, a strain of yeast of known species is treated to obtain chromosomal DNA substantially free of nonchromosomal material. The purified chromosomal DNA is treated to separate at least one chromosome from other chromosomes. Procedures for separating chromosomes include gel electrophoresis as discussed above. A recommended method is CHEF gel electrophoresis. The separated chromosome is isolated, for example, by excising it from the gel, to obtain an isolate of chromosomal DNA which corresponds to substantially the entire DNA sequence of a chromosome. The phrase "which corresponds to substantially the entire DNA sequence of a chromosome" is used herein to mean that the isolate has the entire DNA sequence of the chromosome or has sequences which differ only due to chromosome length polymorphism.

The isolate of chromosomal DNA is treated using standard methods, e.g., heat denaturation, to denature the double-stranded chromosomal DNA to yield single-stranded DNA templates. The templates are randomly primed with short chain primers in the presence of DNA polymerase and a nucleotide mixture to produce a probe which comprises a mixture of random-size copies of DNA molecules.

DNA polymerase refers to an enzyme which synthesizes double-stranded DNA from single-stranded DNA, e.g., Klenow fragment of DNA Polymerase I. Short chain primers refers to any short sequence of oligonucleotides, e.g., hexamers, which enables polymerase to carry out DNA synthesis. Nucleotide mixture refers to a mixture of nucloetides required for DNA synthesis, e.g., a mixture of dATP, dGTP, dTTP, and dCTP. The phrase "denature the double-stranded chromosomal DNA" means that the double strands are sufficiently separated to provide access of the short chain primers, DNA polymerase, and nucloetides and permit synthesis of new DNA copied from the templates.

The probe may be suitably labeled by any means known in the art, for example, by using radioactive $^{32}$P-dCTP.

Assay Using the Probe

The probe prepared as described above can be used to assay test samples for conspecificity as follows. A test strain of yeast is treated to obtain a DNA chromosomal isolate which corresponds to substantially the entire DNA sequence of the chromosome. The isolate can be obtained as described above, for example, by separation of chromosomes by CHEF gel electrophoresis.

The DNA chromosomal isolate of the test sample is denatured to sufficiently separate the two strands to permit the probe to hybridize thereto. The denatured probe is contacted with the denatured DNA chromosomal isolate under hybridization conditions such that DNA sequences which are substantially homologous are hybridized. Two DNA sequences are "substantially homologous" when at least 85% (preferably at least about 90%, and most preferably at least about 95%) of the nucloetides match over the length of the DNA sequences.

The hybridization product is separated from the non-hybridized material by washing under conditions of low stringency. The phrase "low stringency" as used herein means 1–2 X sodium chloride and sodium citrate (SSC), 0.1–0.5% sodium dodecyl sulfate (SDS) at 64°–67° C. for ½–2 hours. The detection of the presence or absence of hybridization products is done by known techniques, for example, by autoradiography. The membranes can be rehybridized after probe removal. Surprisingly, the resulting hybridization reaction is species-specific.

In the assay method of the invention, all the DNA chromosomal isolates from a test yeast can be probed simultaneously or sequentially as described above.

The following examples are intended only to further illustrate the invention and are not intended to limit the scope of the invention which is described by the claims.

EXAMPLE 1

Preparation of Probes

Probe Preparation

A well characterized, commercially available strain of *Saccharomyces cerevisiae* in form of agarose inserts (*S. cerevisiae* YNN 295 Laboratorie (Bio-Rad) was used to prepare the probe. The 16 chromosomes of the strain were separated into 15 bands using CHEF gel electrophoresis (200 V, pulsing times 90s for 9 h and 50s for 15 h, 0.9% agarose (Sea Kem ® GTG, FMC Corporation), 0.5 X Tris Borate EDTA buffer (TBE), 14° C. The gel was ethidium bromide stained, and the corresponding bands from 8 lanes were excised and pooled. The DNA was destained, isolated, and purified by using a specially formulated silica matrix that binds single and double stranded DNA without binding DNA contaminants (Geneclean ®, Bio 101, Inc.) After a short denaturation for 2–3 minutes at 95° C. the DNA was randomly primed using the reagent mix (dATP, dGTP, dTTP, dCTP, and random hexadeoxyribonucleotides) and Klenow Fragment from a commercially available oligolabelling kit (Pharmacia LKB Biotecynology AB, Piscataway, N.J.) and $^{32}$P-radiolabeled $^{32}$P dCTP (Amersham). For the labeling reaction 10 µl reaction mix (buffer-primers-nucloetides), 34 µl clean, denatured DNA, 5 µl $^{32}$P dCTP, and 1 µl Klenow fragment of *E. coli* DNA polymerase I were used. The reaction product was passed through a spun column containing beaded agarose (Sephadex ®, Pharmacia LKB Biotechnology AB, Piscataway, N.J.) by centrifuging in a Beckman GPR centrifgue at 750 rpm for 2 minutes. The reaction took one hour at 37° C. After removing the unincorporated nucleotides, the enzyme and the primers, and washing the column with 50 µl distilled water, the probe was stored at −25° C. Immediately before use, the probe was denatured by heating at 95° C. for 2–5 minutes.

EXAMPLE 2

Assay of Test Samples

Yeast Strains

The yeast strains are listed in Table 1. All of the samples were pure yeast cultures.

TABLE 1

| Strain | Origin |
| --- | --- |
| Saccharomyces cerevisiae | NRRL Y-12632[T,a] |
| Saccharomyces cerevisiae | NRRL Y-2034 |
| Saccharomyces cerevisiae | YNN 295[b] |
| Saccharomyces cerevisiae | D 101[c] |
| Saccharomyces cerevisiae | D 105 |
| Saccharomyces cerevisiae | Y 180 |
| Zygosaccharomyces bailii | NRRL Y-2227[T] |
| Zygosaccharomyces bailii | NRRL Y-7261 |
| Zygosaccharomyces bisporus | NRRL Y-12626[T] |
| Zygosaccharomyces bisporus | NRRL Y-7253 |
| Zygosaccharomyces rouxii | NRRL Y-229[T] |
| Zygosaccharomyces rouxii | NRRL Y-2547 |
| Zygosaccharomyces rouxii | NRRL Y-2548 |

[a]Type strain (T) of the species
[b]Yeast chromosome size standard (Bio-Rad)
[c]Strains isolated from processed fruits Sample Preparation and CHEF Electrophoresis The yeast cultures were grown overnight in YPD (1% yeast extract, 1% glucose, and 2% Batco peptone) at 26° C. The cells were harvested by centrifugation, washed twice with 125 mM EDTA, pH 7.5, and treated with cell wall degrading enzyme (Lyticase, Sigma Chemical Company, St. Louis, Mo.) (50 units/ml; stock solution 10 units/μl in 50% v/v glycerol-TE, stored at −25° C.) in 50 mM EDTA, pH 7.5 for 30 minutes at 37° C. Two ml of the "Lyticase"-treated cell suspension was then mixed with 2 ml 2% agarose (SeaKem® GTG, FMC Corporation) (prepared in 0.5 X TBE), and the mixture was formed into agarose plugs using a mold sold by Bio-Rad Laboratories. The agarose plugs solidified for 10 minutes at 4° C. The inserts were kept overnight at 37° C. in an Erlenmeyer flask containing 20 ml 50 mM EDTA, pH 8.0 with 0.15% Tris and 7.5% 2-mercaptoethanol. The next day, the agarose plugs were transferred into an Erlenmeyer flask containing 10 ml ES buffer (50 mM EDTA, 1% N-laurylsarcosine), pH 9.5 with 1 mg/ml protein degrading enzyme (Proteinase K, Boeringer-Mannheim Corporation) (stock solution 10 mg/ml in 50% glycerol-TE, stored at −25° C.) and incubated overnight at 50° C. The plugs were rinsed 3 times with 50 mM EDTA, washed 3 times for 1.5 hours each with 50 mM EDTA and stored in 50 mM EDTA at 4° C.

CHEF gel electrophoresis of Saccharomyces strains was carried out at 200 V, pulsing times 120s for 9 h and 50 s for 15 h, 0.9% agarose (SeaKem® GTG, FMC Corporation), 0.5 X TBE, 14° C.

CHEF gel electrophoresis of Zygosaccharomyces strains was carried out at 125 V, ramping from 600s to 120s for 24 h, followed by the same parameters used for the Saccharomyces strains for the second 24 h using 0.8% agarose.

After CHEF gel electrophoresis the gels were stained with ethidium bromide and photographs were taken using Polaroid® 57 or Polaroid® 55 film with shortwave UV illumination.

DNA was then transferred to a positively charged nylon membrane (GeneScreen Plus™, E. I. du Pont de Nemours and Company) as described by Maniatis et al. (Molecular Cloning. A Laboratory Manual, Cold Spring Harbor Laboratory, Cold Spring Harbor, 1982). After depurination with 0.25 HCl for 5–15 minutes, we used 0.4N NaOH for capillary transfer of DNA to the nylon membrane. The membrane was then washed for 20 minutes in 200 mM Tris, pH 7.5 and 2 X SSC and and dried at 65° C. After 15 minutes prehybridization with 25–35 ml hybridization mixture at 65° C., hybridization took place overnight at the same temperature (hybridization solution: 1M NaCl, 1% SDS, 10% dextran sulfate, 100–200 μg/ml sonicated salmon sperm DNA (stock solution 10 mg/ml) and 50 μl denatured radioactive probe added in the Seal-A-Meal® (Dazey Corporation) bag).

The next day, the membrane was washed twice in 2 X SSC, 0.1% SDS for 30 minutes at 65° C. Autoradiographs were made with X-OMAT ™ AR film (Eastman Kodak Company) at −80° C. for 3 h to 1 week. In order to reuse membranes for hybridization, the radioactive DNA probe was removed by ½ hour boiling in 0.1 X SSC, 1% SDS.

Results

Figure 1:
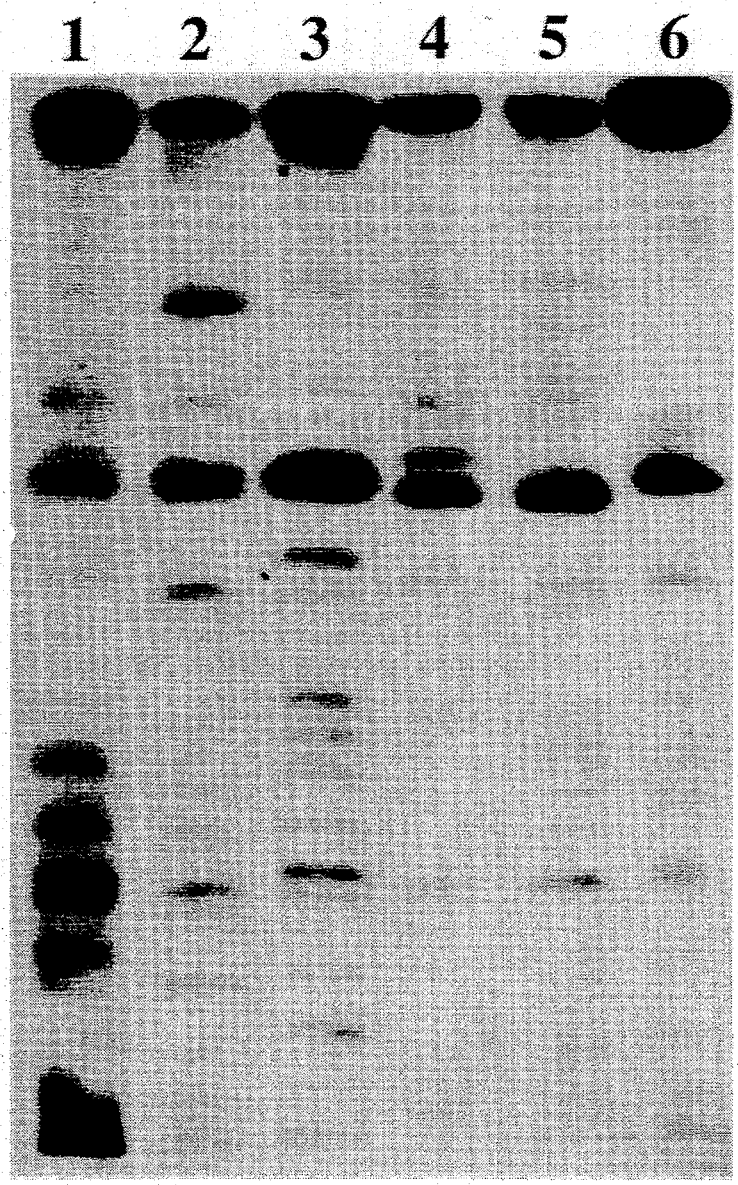
FIG. 1 is a Southern blot showing hybridization reaction between target chromosomes XV and VII of different *S. cerevisiae* strains and the probe which was prepared by using the same chromosomes of the yeast chromosome size standard (*S. cerevisiae* YNN 295).

FIG. 1 shows that all the strains tested belong to the same species. FIGS. 2A and 2B show that in lane 6 the sample DNA had no homology to the probe, proving that it was a different species. FIGS. 3A and 3B show that in lanes 2–8 the sample DNA had no homology to the probes, proving that they were different species.

It is understood that the foregoing detailed description is given merely by way of illustration and that modification and variations may be made therein without departing from the spirit and scope of the invention.

We claim:

1. A method for assaying a test sample for conspecificity in lower eukaryotes selected from the group consisting of yeasts and molds, comprising:
   (a) providing an isolate of double-stranded chromosomal DNA corresponding to substantially the entire DNA sequence of a chromosome in a yeast or mold;
   (b) denaturing said double-stranded chromosomal DNA to yield single-stranded DNA templates corresponding to substantially the entire DNA sequence of said chromosome;
   (c) random priming said single-stranded DNA templates with short chain primers in the presence of DNA polymerase and a nucleotide mixture to produce a probe which comprises a mixture of random-size copies of DNA molecules, said probe containing the DNA sequence information of substantially said entire chromosome;
   (d) contacting a test sample comprising a separated, denatured chromosome with said probe under hybridization conditions such that DNA sequences in the test sample which are substantially homologous with said probe are hybridized to produce a hybridization product;
   (e) separating said hybridization product from unhybridized material by washing under conditions of lower stringency; and
   (f) analyzing for said hybridization product.

2. The method of claim 1 wherein said probe is radiolabeled.

3. A method for assaying a test sample for conspecificity in lower eukaryotes selected from the group consisting of yeasts and molds, comprising:

(a) contacting a test sample comprising a separated, denatured chromosome a probe prepared by denaturing an isolated chromosomal DNA corresponding to substantially the entire DNA sequence of a chromosome in a yeast and mold to yield single stranded DNA templates and random priming said single-stranded DNA templates with short chain primers in the presence of DNA polymerase and nucleotide mixture to produce a probe which comprises a mixture of random-size copies of DNA molecules, said probe containing the DNA sequence information of substantially said entire chromosome and hybridizing under hybridization conditions such that DNA sequences in the test sample which are substantially homologous with said probe are hybridized to produce a hybridization product;

(e) separating said hybridization product from unhybridized material by washing under conditions of low stringency; and (f) analyzing for said hybridization product.

* * * * *